US012691001B2

(12) United States Patent (10) Patent No.: US 12,691,001 B2
Simpson et al. (45) Date of Patent: Jul. 28, 2026

(54) SELF-RETAINING OCCLUSAL SPLINT

(71) Applicant: KLS Martin, L.P., Jacksonville, FL (US)

(72) Inventors: Travis Simpson, Jacksonville, FL (US); Elliott Pearson, Jacksonville, FL (US)

(73) Assignee: KLS MARTIN, L.P., Jacksonville, FL (US)

( * ) Notice: Subject to any disclaimer, the term of this patent is extended or adjusted under 35 U.S.C. 154(b) by 80 days.

(21) Appl. No.: 18/632,157

(22) Filed: Apr. 10, 2024

(65) Prior Publication Data

US 2024/0335318 A1 Oct. 10, 2024

Related U.S. Application Data

(60) Provisional application No. 63/458,383, filed on Apr. 10, 2023.

(51) Int. Cl.
*A61F 5/56* (2006.01)
(52) U.S. Cl.
CPC ................................... *A61F 5/566* (2013.01)

(58) Field of Classification Search
CPC ....... A61F 5/56–566; A61C 7/08; A61C 7/36; A63B 71/085; A63B 2071/086; A63B 2071/088; Y10S 602/902; A61B 90/16; A61B 1/24
See application file for complete search history.

(56) References Cited

U.S. PATENT DOCUMENTS

2016/0074207 A1* 3/2016 Choi ........................ A61F 5/566
 128/848
2023/0270527 A1* 8/2023 Kim ......................... A61C 7/08
 433/6

* cited by examiner

*Primary Examiner* — Alireza Nia
*Assistant Examiner* — Robin Han
(74) *Attorney, Agent, or Firm* — Thomas C. Saitta

(57) ABSTRACT

An occlusal splint having an occlusal plate portion, two sets of exterior prong members and two sets of interior prong members disposed on the occlusal plate to define a pair of channels to receive the upper and lower dental arches, the prong members configured to match either the interdental regions or the central crown regions of the teeth. The prong members are composed of a material allowing the prong members to flex when the splint is mounted onto the dental arches and then rebound to provide a biasing force against the teeth to retain the splint on the dental arches.

1 Claim, 7 Drawing Sheets

SELF-RETAINING OCCLUSAL SPLINT

BACKGROUND OF THE INVENTION

This application relates to dental splints, and more particularly relates to occlusal splints or similar dental registration devices.

An occlusal splint or orthotic device is a specially designed mouth guard for people who grind their teeth, have a history of pain and dysfunction associated with their bite or temporomandibular joints (TMJ), or have completed a full mouth reconstruction. An occlusal splint is configured to cover the incisal and occlusal surfaces of one or both dental arches to stabilize the teeth, treat bruxism, or facilitate proper occlusal positioning. Occlusal surfaces are the surfaces of the teeth that contact the surfaces of the opposing teeth during biting or chewing.

Common occlusal splints are made from a processed acrylic resin. In addition to acrylic resins, occlusal splints may be manufactured from thermoplastics, alone or in combination with hard acrylic resins. Thermoplastics may provide greater flexibility to drastically improve patient comfort while being sufficiently rigid to maintain its shape during use. Thermoplastic dental splints may also deliver superior contouring ability, which further improves patient comfort and ensures a more precise fit.

CAD/CAM milling and more recently 3D printing, in association with computer-aided design, now provide much more precise contouring for occlusal splints and provide patient-specific, customized occlusal splints. Once the digital splint design is approved, the dental splints are milled from a solid block of thermoplastic material or 3D printed.

Typical occlusal splints are generally horseshoe shaped or U-shaped and are designed to cover the entire or substantially most of the anterior and lingual surfaces of the teeth in addition to the occlusal surfaces, i.e., to cover the entire exposed crown of the tooth. This can be a problem where access to tooth surfaces is needed for cleaning or affixation of other devices. In addition, many of the known occlusal splints must be held in place by wiring the splint to multiple teeth.

It is an object of this invention to provide an improved occlusal splint wherein the splint minimizes coverage of the tooth surface and does not require wiring of the splint to the teeth. It is an object to provide such a splint wherein the splint is configured with flexible prong members that allow the splint to be snap fit (i.e., biased) onto the teeth so as to be self-retaining, the prong members being disposed interdentally, for increased exposure of the anterior and lingual crown surfaces or disposed partially on the anterior and lingual crown surfaces, for increased exposure of the interdental regions.

BRIEF SUMMARY OF THE INVENTION

In brief summary, the invention is a customized occlusal splint that is self-retaining on a patient's teeth, i.e., does not require adhesives, wires or other mechanical fixation means for this purpose. The occlusal splint is sized, shaped, configured and produced in known manner using computer aided design methodologies based on CT or other imaging scans of the patient, such that the splint is patient specific.

The occlusal splint comprises a generally U- or horseshoe-shaped plate portion sized and configured to be disposed between the occlusal surfaces of the upper and lower teeth. The arch of the plate portion conforms to the dental arches of the patient, and the upper and lower surfaces of the plate contain tooth recesses conforming to the occlusal surfaces of the patient's teeth.

A plurality of exterior or anterior prong members and a plurality of lingual or interior prong members extend upward from the plate to abut portions of the anterior and lingual surfaces of the upper teeth and a plurality of exterior or anterior prong members and a plurality of lingual or interior prong members extend downward from the plate to abut portions of the anterior and lingual surfaces of the lower teeth. In one embodiment of the splint, the prong members abut the interdental surfaces of the teeth, leaving most of the anterior and lingual surfaces of the teeth exposed. In a second embodiment, the prong members abut the central portions of the anterior and lingual surfaces of the teeth, leaving the interdental surfaces exposed.

The prongs are structured such that they must be biased or flexed outwardly when the occlusal splint is mounted onto the teeth, the chosen material of construction and the design allowing the prongs to bias or flex back to a more neutral position such that the splint is self-retaining on the teeth, but readily removable as needed.

DETAILED DESCRIPTION OF THE INVENTION

Figure 1:
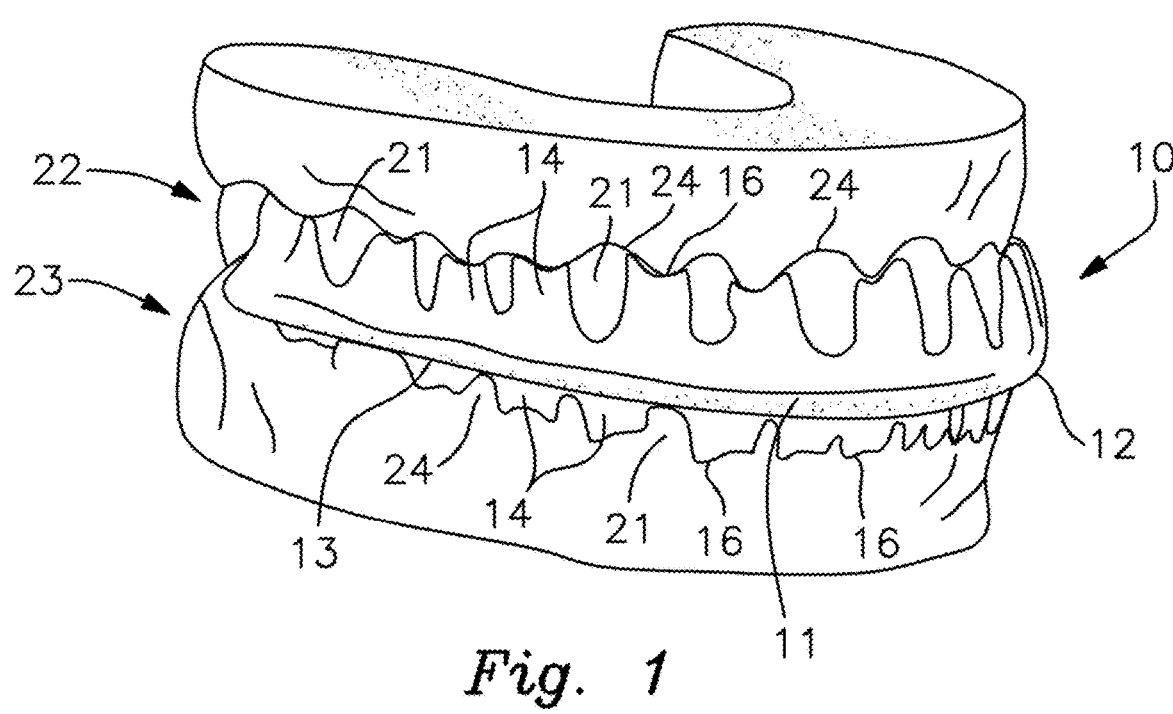
FIGS. 1 and 2 illustrate two anterior views of an occlusal splint disposed on a computer model of the upper and lower dental arch of a patient, wherein the flexible prongs are positioned interdentally to expose the central surfaces of the teeth.

With reference to the drawings, embodiments of the self-retaining occlusal splint will now be set forth in detail, it being understood that the drawings are provided for illustrative purposes and are not meant to be limiting as to the scope of the invention. The dental arches and teeth shown in the drawings are computer designed models which match the actual dental arches and teeth of the patient for which the occlusal splint is intended.

In general, the invention in various embodiments is a customized, patient-specific occlusal splint 10 that is self-retaining on the teeth 21 of the patient. The splint 10 is formed of a relatively rigid polymer that possesses sufficient rigidity whereby certain elements of the splint 10, specifically the prong members 14/15, will return toward or to the non-flexed position after being biased or flexed outwardly to position the splint on the teeth 10 of the patient.

Figure 2:
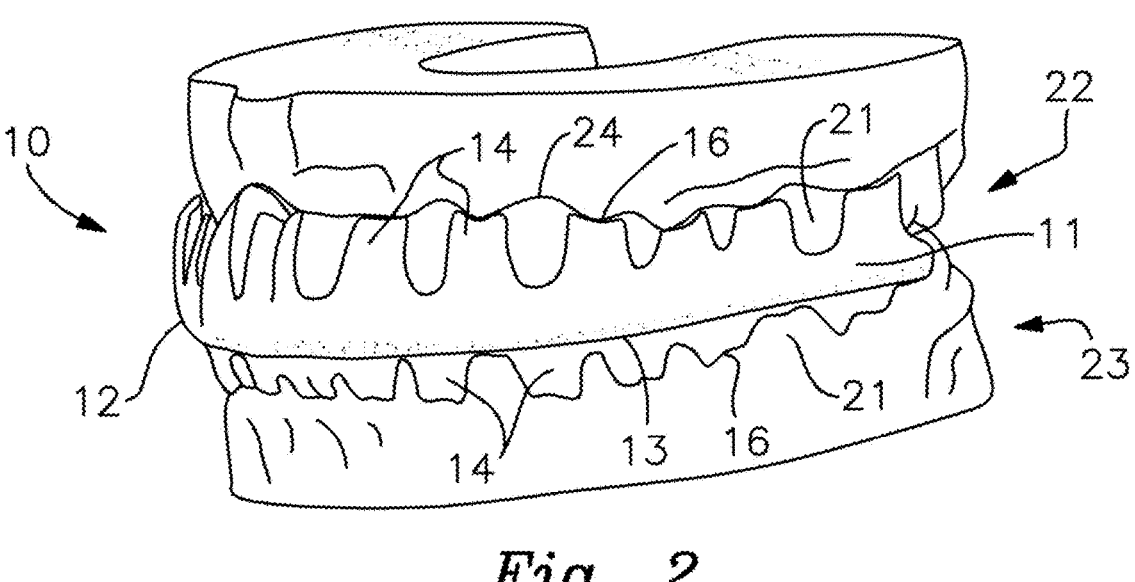
Figure 3:
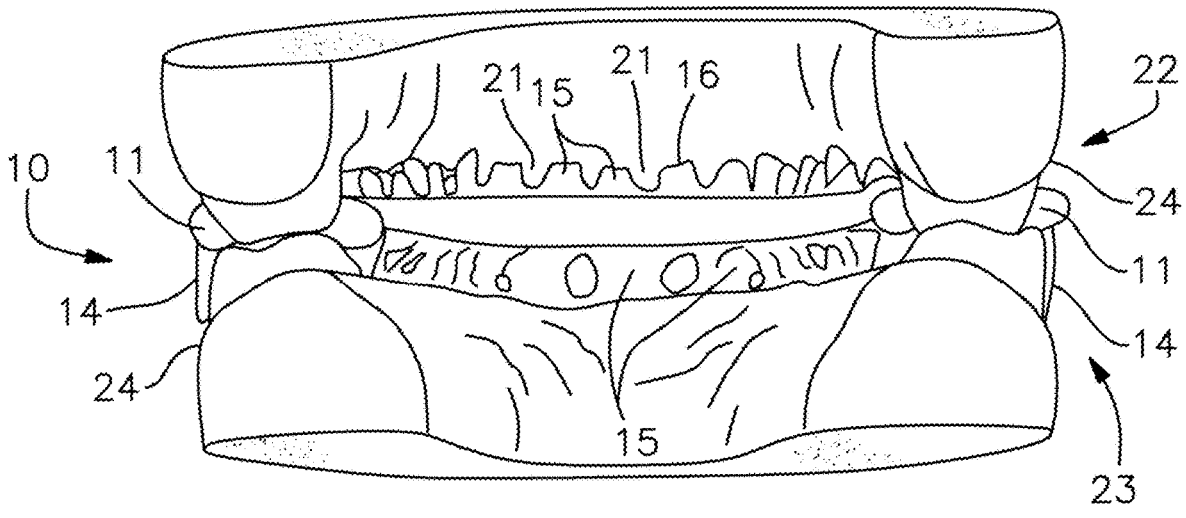
FIG. 3 is a posterior view of the occlusal splint of FIGS. 1 and 2 shown disposed on the computer model of the upper and lower dental arch of the patient.
Figure 7:
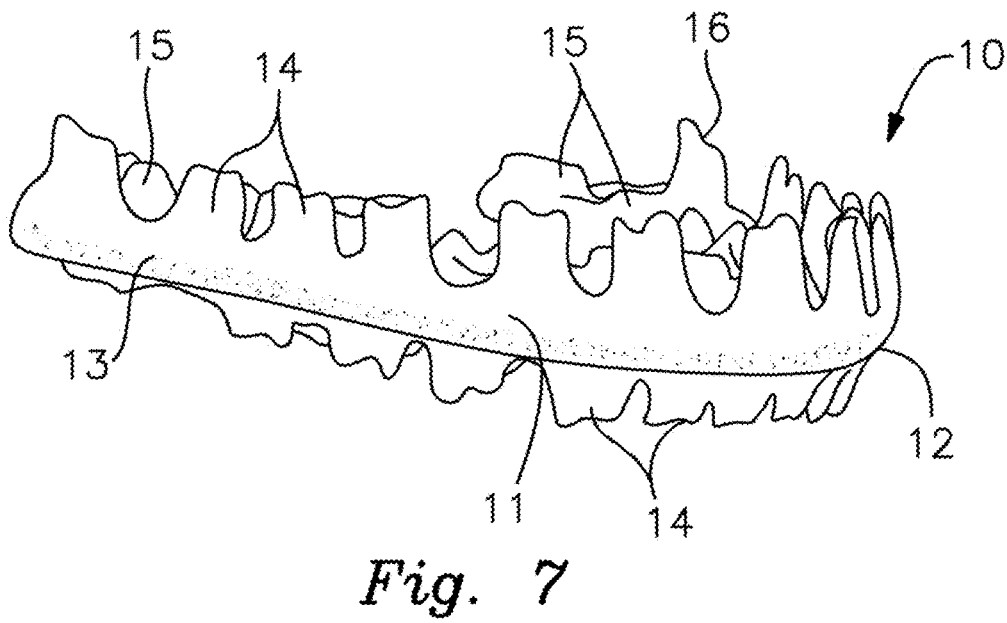
FIGS. 7 and 8 illustrate two anterior views of the occlusal splint of FIGS. 1 and 2.
Figure 8:
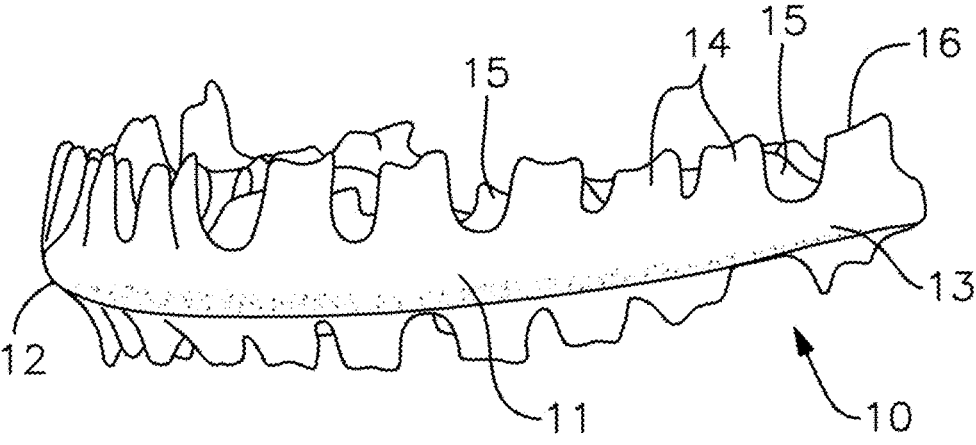
Figure 9:
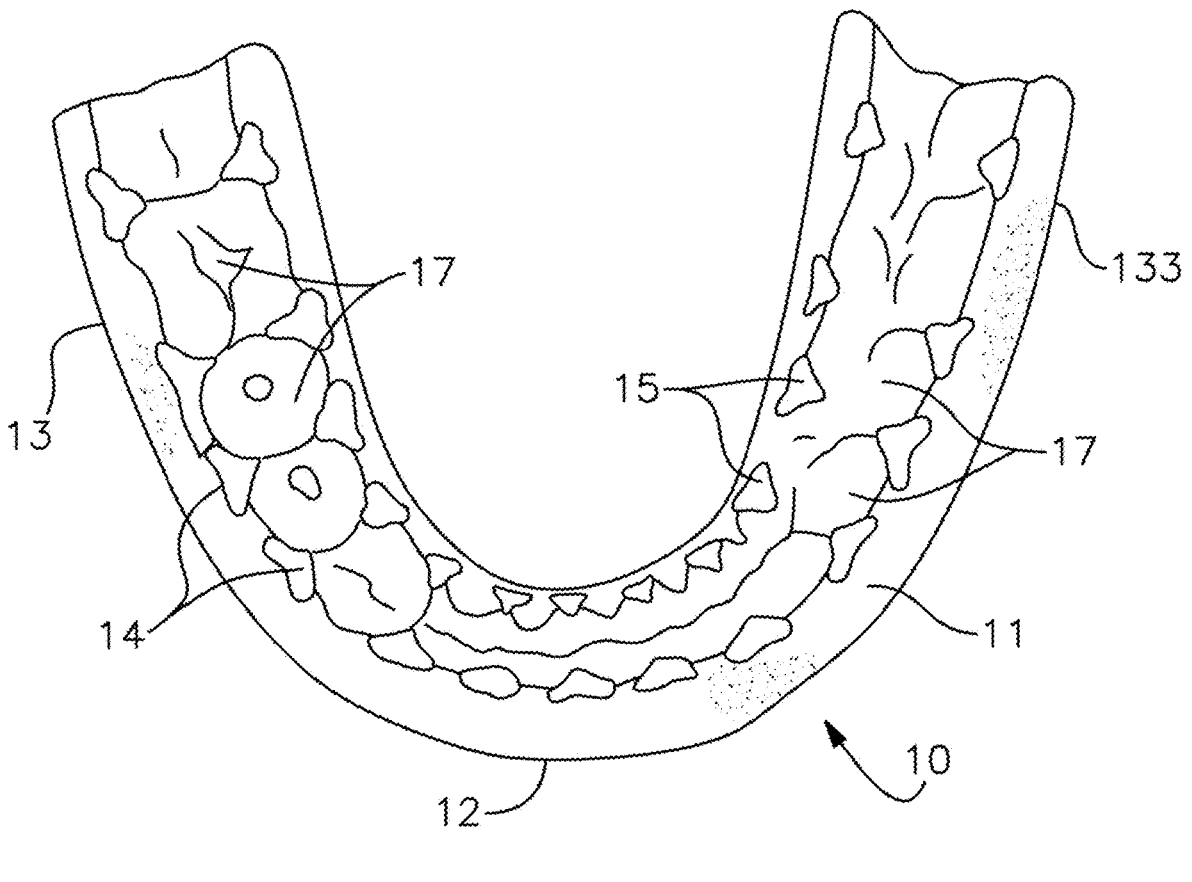
FIG. 9 illustrates a view of the upper side of the occlusal splint of FIGS. 7 and 8, showing the anterior and lingual prongs and the tooth recesses formed in the plate.

A first embodiment of the self-retaining occlusal splint is shown in FIGS. 1-3 and 7-9. The occlusal splint 10 comprises an occlusal plate or body 11 configured generally in a horseshoe or U-shape, the occlusal plate 11 having an anterior or frontal portion 12 and two lateral or side portions 13 so as to extend around most or all of the upper dental arch 22 and the lower dental arch 23. The occlusal plate 11 is the body of material disposed between the occlusal surfaces of the teeth 21 when in use.

The occlusal plate 11 is configured thorough computer-aided design to match the configuration of the occlusal surfaces of the teeth 21, the upper and lower surfaces of the plate 11 containing tooth recesses 12 conforming to the occlusal surfaces of the patient's teeth 21, such that the occlusal plate 11 receives and mates with the occlusal surfaces of each of the teeth 21 when the splint 10 is worn. The occlusal splint 10 is provided with a plurality of exterior or anterior prong members 14 and a plurality of lingual or interior prong members 15, each exterior prong member 14 being paired with a corresponding interior prong member 15.

One set of the exterior prong members 14 extends upward from the occlusal plate 11 and another set of the exterior prong members 14 extends downward from the occlusal plate 11. Both sets of exterior prong members 14 are disposed in a horseshoe or U-shaped configuration. The exterior prong members 14 are each configured thorough computer-aided design to match the configuration of the corresponding anterior interdental area between two adjacent teeth 21. Thus, the configuration of each exterior prong member 14 is unique. The interior surface of each exterior prong member 14 will have a generally convex or outwardly angular profile which abuts the lateral surfaces of a pair of adjoining teeth 21. The exterior prong members 14 are configured to have little or no contact with the gums 24, and the width of the prong members 14 are minimized as much as possible to reduce the area of contact with the teeth 21.

One set of the interior prong members 15 extends upward from the occlusal plate 11 and another set of the interior prong members 15 extends downward from the occlusal plate 11. Both sets of interior prong members 15 are disposed in a horseshoe or U-shaped configuration. The interior prong members 15 are each configured thorough computer-aided design to match the configuration of the corresponding lingual interdental area between two adjacent teeth 21. Thus, the configuration of each interior prong member 15 is unique. The interior surface of each interior prong member 15 will have a generally convex or outwardly angular profile which abuts the lateral interior surfaces of a pair of adjoining teeth 21. The interior prong members 15 are configured to have little or no contact with the gums 24, and the width of the prong members 15 are minimized as much as possible to reduce the area of contact with the teeth 21.

The combination of the occlusal plate 11, the exterior prong members 14 and the interior prong members 15 define a pair of U-shaped channels, one channel extending upwardly from the occlusal plate 11 to receive and retain the teeth 21 of the upper dental arch 22 and the other channel extending downwardly from the occlusal portion to receive and retain the teeth 21 of the lower dental arch 23.

The material of composition and configuration design for the exterior prong members 14, is such that each of the prong members 14 is characterized in having a limited or controlled amount of outward flex or bias which enables the splint 10 to be snapped onto the upper and lower dental arches 22/23, yet still maintain the splint 10 securely on the dental arches 22/23. This is possible because the exterior surfaces of the teeth 21 are convex in the vertical direction, such that the teeth 21 are narrower in the area near the gums 24. Because the prong members 14 are configured to match the configurations of the exterior and interior surfaces of the teeth 21, the prong members 14 are generally concave or bent in the vertical direction, such that free ends 16 of the prong members 14 are inwardly oriented. When the splint 10 is placed onto the teeth 21, the free ends 16 of the prong members first flex outwardly to pass over the broader midportion of the tooth 21 and then flex back inwardly to cradle the tooth 21. Preferably the prong members 14 are configured such that they do not completely return to their relaxed, i.e., non-flexed, position, but instead provide a biasing force against the teeth 21 to better retain the splint 10 on the teeth 21.

Figure 4:
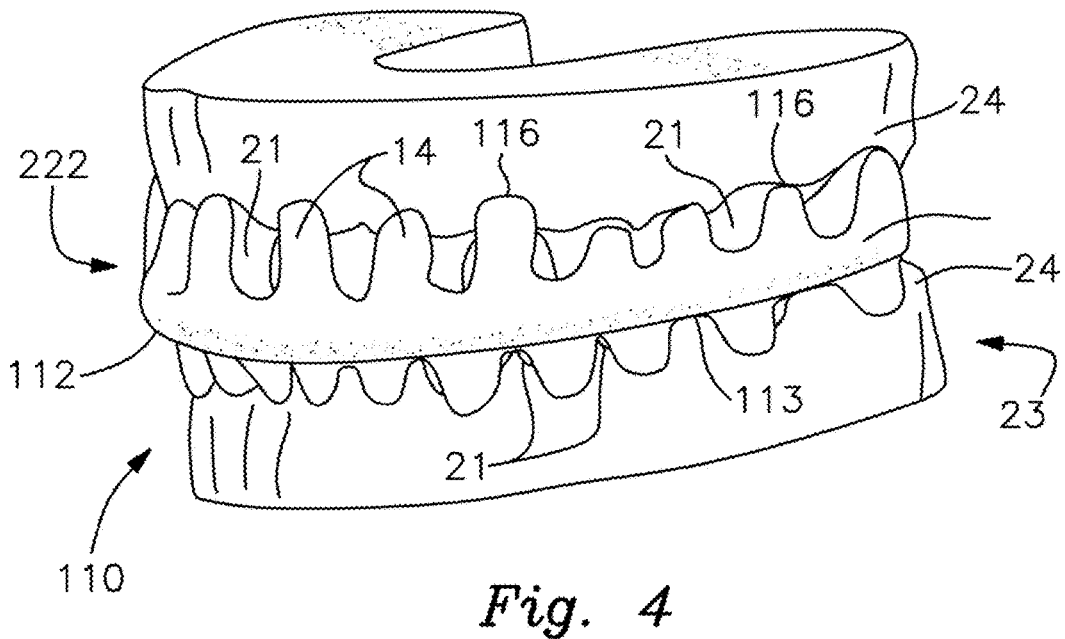
FIGS. 4 and 5 illustrate two anterior views of an occlusal splint disposed on a computer model of the upper and lower dental arch of a patient, wherein the flexible prongs are positioned on the central portions of anterior and lingual crown surfaces to expose the interdental surfaces.
Figure 5:
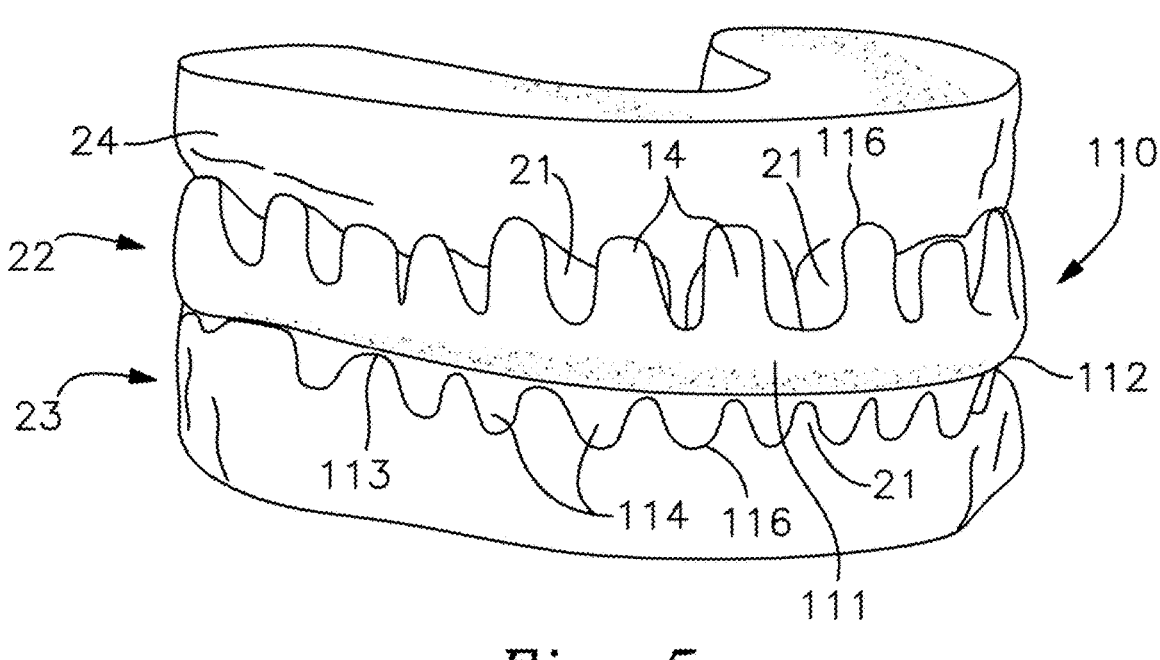
Figure 6:
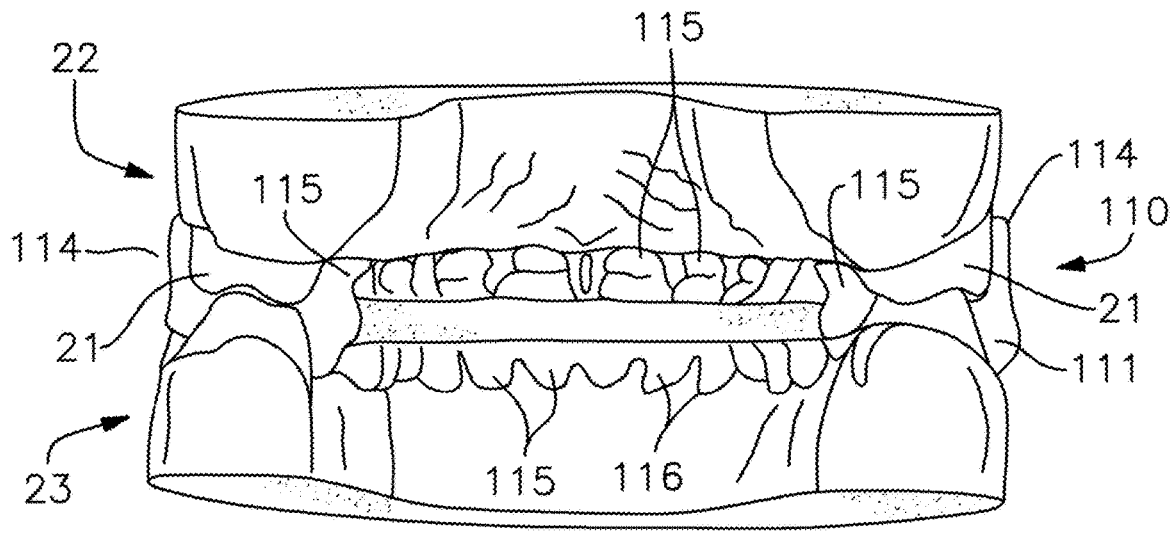
FIG. 6 is a posterior view of the occlusal splint of FIGS. 4 and 5 shown disposed on the computer model of the upper and lower dental arch of the patient.
Figure 10:
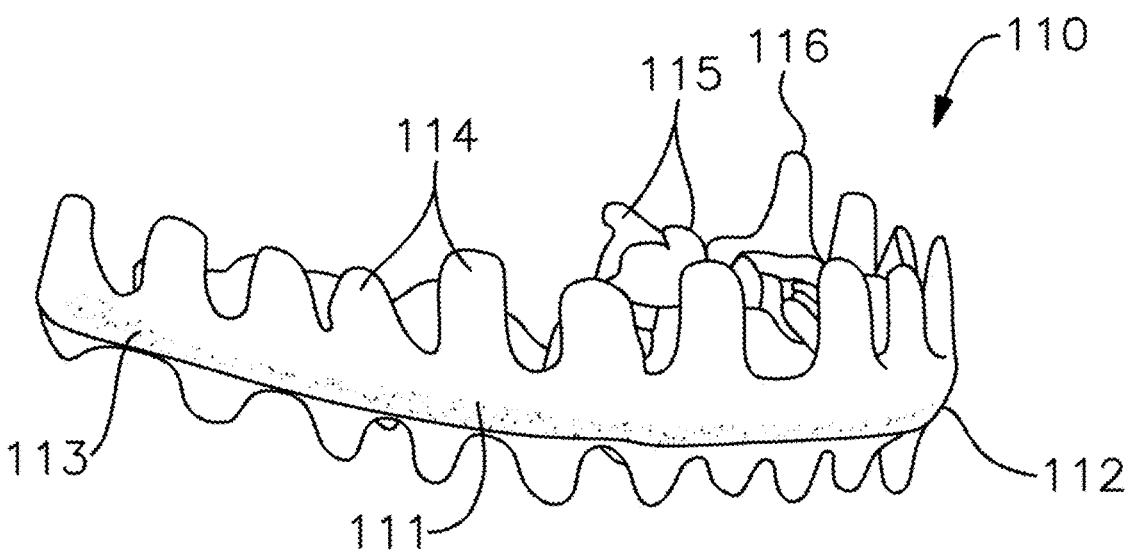
FIGS. 10 and 11 illustrate two anterior views of the occlusal splint of FIGS. 4 and 5.
Figure 11:
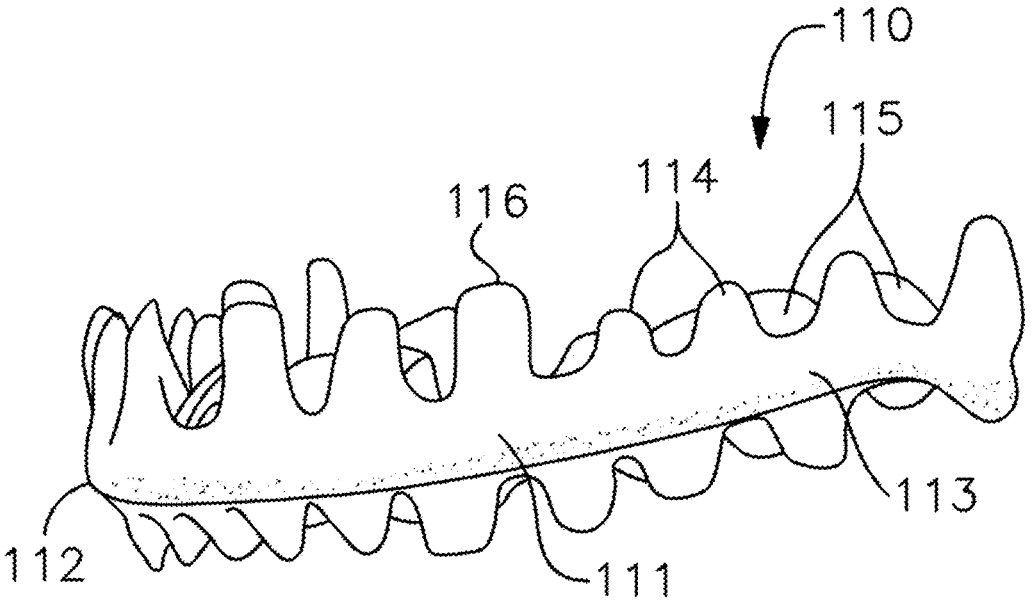
Figure 12:
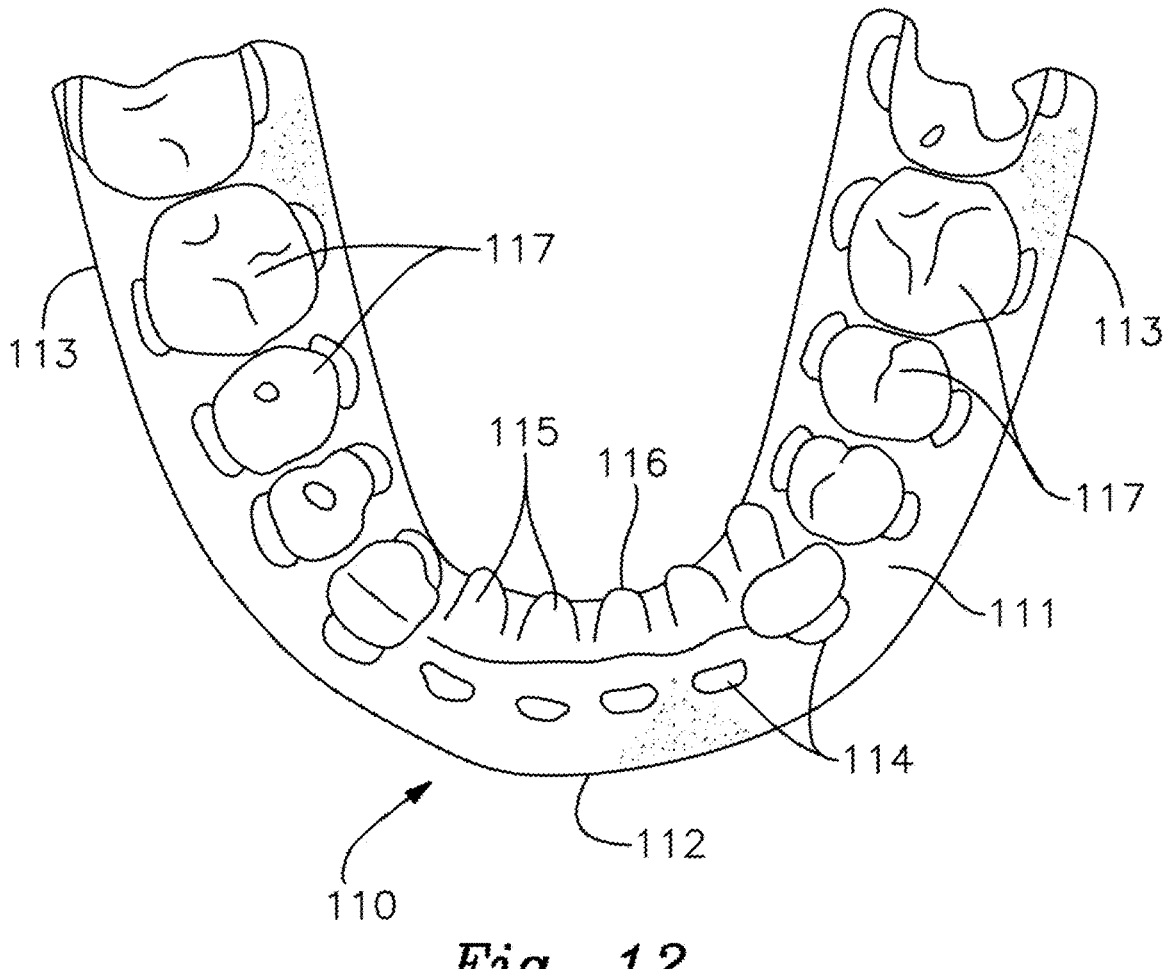
FIG. 12 illustrates a view of the upper side of the occlusal splint of FIGS. 10 and 11, showing the anterior and lingual prongs and the tooth recesses formed in the plate.

In an alternative embodiment shown in FIGS. 4-6 and 10-12, the prongs 114/115 of the occlusal splint 100 are disposed on the central exterior and central interior crown surfaces of the teeth 21 rather than being interdentally spaced. The occlusal splint 110 comprises an occlusal plate or body 111 configured generally in a horseshoe or U-shape, the occlusal plate 111 having an anterior or frontal portion 112 and two lateral or side portions 113 so as to extend around most or all of the upper dental arch 22 and the lower dental arch 23. The occlusal plate 111 is the body of material disposed between the occlusal surfaces of the teeth 21 when in use. Tooth recesses 117 are disposed on the upper and lower surfaces of the occlusal plate 11, which match and receive the occlusal portions of the teeth 21.

One set of the exterior prong members 114 extends upward from the occlusal plate 111 and another set of the exterior prong members 114 extends downward from the occlusal plate 111. Both sets of exterior prong members 114 are disposed in a horseshoe or U-shaped configuration. The exterior prong members 114 are each configured thorough computer-aided design to match the configuration of the central exterior crown portion of the corresponding tooth 21. Thus, the configuration of each exterior prong member 114 is unique. The interior surface of each exterior prong member 114 will have a generally concave profile which abuts the central crown portion of a tooth 21. The exterior prong members 114 are configured to have little or no contact with the gums 24, and the width of the prong members 114 are minimized as much as possible to reduce the area of contact with the teeth and completely expose the interdental surfaces between adjacent teeth 21.

One set of the interior prong members 115 extends upward from the occlusal plate 111 and another set of the interior prong members 115 extends downward from the occlusal plate 111. Both sets of interior prong members 115 are disposed in a horseshoe or U-shaped configuration. The interior prong members 115 are each configured thorough computer-aided design to match the configuration of the interior central crown portion of the corresponding tooth 21. Thus, the configurations of each interior prong member 115 is unique. The interior surface of each interior prong member 115 will have a generally concave profile which abuts the central crown portion of the tooth 21. The interior prong members 115 are configured to have little or no contact with the gums 24, and the width of the prong members 115 are minimized as much as possible to reduce the area of contact with the teeth 21 and completely expose the interdental surfaces between adjacent teeth 21.

The combination of the occlusal plate 111, the exterior prong members 114 and the interior prong members 115 define a pair of U-shaped channels, one channel extending upwardly from the occlusal plate 111 to receive and retain the teeth 21 of the upper dental arch 22 and the other channel extending downwardly from the occlusal portion to receive and retain the teeth 21 of the lower dental arch 23.

The material of composition and configuration design for the exterior prong members 114, is such that each of the prong members 114 is characterized in having a limited or controlled amount of flex or bias which enables the splint 110 to be snapped onto the upper and lower dental arches 22/23, yet still maintain the splint 110 securely on the dental arches 22/23. This is possible because the exterior surfaces of the teeth 21 are convex in the vertical direction, such that the teeth 21 are narrower in the area near the gums 24. Because the prong members 114 are configured to match the configurations of the exterior and interior surfaces of the teeth 21, the prong members 114 are generally concave or bent in the vertical direction, such that free ends 116 of the prong members 114 are inwardly oriented. When the splint 110 is placed onto the teeth 21, the free ends 116 of the prong members 114 first flex outwardly to pass over the broader midportion of the tooth 21 and then flex back inwardly to cradle the tooth 21. Preferably the prong members 14 are configured such that they do not return to their relaxed, i.e., non-flexed, position, but instead provide a biasing force against the teeth 21 to better retain the splint 110 on the teeth.

As described, the invention is a self-retaining occlusal splint 10/100 adapted to secure teeth 21 in an upper and lower dental arch 22/23 of a patient in a fixed, occluded relationship, the self-retaining occlusal splint 10/100 being patient-specific and comprising: a horseshoe-shaped occlusal plate 11/111 having an upper surface and a lower surface; tooth recesses 17/117 disposed on the upper and lower surfaces of the occlusal plate 11/111, each of the tooth recesses 17/117 adapted to receive and mate with the occlusal surface of an individual tooth 21 in an upper and a lower dental arch 22/23; an upper set of exterior prong members 14/114 and an upper set of interior prong members 15/115 disposed on the upper surface of the occlusal plate 11/111, wherein each of the exterior prong members 14/114 of the upper set of exterior prong members is paired with an interior prong member 15/115 of the upper set of interior prong members, such that in combination the paired exterior and interior prong members 14/15/114/115 are adapted to receive teeth 21 of an upper dental arch 22; and a lower set of exterior prong members 14/114 and a lower set of interior prong members 15/115 disposed on the lower surface of the occlusal plate 11/111, wherein each of the exterior prong members 14/114 of the lower set of exterior prong members is paired with an interior prong member 15/115 of the lower set of interior prong members, such that in combination the paired exterior and interior prong members 14/15/114/115 are adapted to receive teeth 21 of a lower dental arch 23; wherein the material of composition of the exterior and interior prong members 14/15/114/115 is such that the exterior and interior prong members 14/15/114/115 are outwardly flexible under a bias into a flexed position, but will return toward an unflexed position when the bias is removed to retain the occlusal splint 10/100 on the teeth 21.

Furthermore, an embodiment of the invention further comprises such a self-retaining occlusal splint 10/100, wherein the upper and lower exterior prong members 14/114 and the upper and lower interior prong members 15/115 are positioned along the occlusal plate 11/111 whereby they are adapted to align with an interdental space between adjacent teeth 21 such that a central portion of each tooth 21 is exposed. Another embodiment of the invention further comprises a self-retaining occlusal splint, wherein the upper and lower exterior prong members 14/114 and the upper and lower interior prong members 15/115 are positioned along the occlusal plate 11/111 whereby they are adapted to align with a central portion of each tooth 21 such that an interdental space between adjacent teeth 21 is exposed.

It is understood that equivalents and substitutions for certain elements set forth above may be obvious to those of skill in the art, and therefore the true scope and definition of the invention is to be as set forth in the following claims.

We claim:

1. A self-retaining occlusal splint adapted to secure teeth in an upper and lower dental arch of a patient in a fixed, occluded relationship, the self-retaining occlusal splint configured to be patient-specific and comprising:

a horseshoe-shaped occlusal plate having an upper surface and a lower surface;

tooth recesses disposed on the upper and lower surfaces of the occlusal plate, each of the tooth recesses adapted to receive and mate with an occlusal surface of an individual tooth in the upper and lower dental arch;

an upper set of exterior prong members and an upper set of interior prong members disposed on the upper surface of the occlusal plate, wherein each of the exterior prong members of the upper set of exterior prong members is paired with an interior prong member of the upper set of interior prong members, such that in combination the paired exterior and interior prong members are adapted to receive the teeth of the upper dental arch;

a lower set of exterior prong members and a lower set of interior prong members disposed on the lower surface of the occlusal plate, wherein each of the exterior prong members of the lower set of exterior prong members is paired with an interior prong member of the lower set of interior prong members, such that in combination the paired exterior and interior prong members are adapted to receive the teeth of the lower dental arch;

wherein a material of composition of the exterior and interior prong members is such that the upper and lower set of exterior and interior prong members are outwardly flexible under a bias into a flexed position, but will return toward an unflexed position when the bias is removed to retain the occlusal splint on the teeth;

wherein the upper and lower exterior prong members and the upper and lower interior prong members are positioned along the occlusal plate whereby they are adapted to be directly aligned within an interdental space between adjacent teeth such that a central portion of a tooth is exposed between adjacent upper exterior prong members, a central portion of a tooth is exposed between adjacent lower exterior prong members, a central portion of a tooth is exposed between adjacent upper interior prong members, and a central portion of a tooth is exposed between adjacent lower interior prong members.

* * * * *